(12) United States Patent
Grobbee et al.

(10) Patent No.: US 10,389,333 B2
(45) Date of Patent: Aug. 20, 2019

(54) REMOVABLE SYSTEM AND METHOD FOR DENTURES AND SURGICAL GUIDES

(71) Applicant: Global Dental Science LLC, Scottsdale, AZ (US)

(72) Inventors: Johannes Petrus Michael Grobbee, Oosterbeek (NL); Timothy C. Thompson, Fountain Hills, AZ (US)

(73) Assignee: Global Dental Science LLC, Scottsdale, AZ (US)

( * ) Notice: Subject to any disclaimer, the term of this patent is extended or adjusted under 35 U.S.C. 154(b) by 0 days.

(21) Appl. No.: 14/768,742

(22) PCT Filed: Feb. 19, 2014

(86) PCT No.: PCT/US2014/017136
§ 371 (c)(1),
(2) Date: Aug. 18, 2015

(87) PCT Pub. No.: WO2014/130536
PCT Pub. Date: Aug. 28, 2014

(65) Prior Publication Data
US 2016/0000536 A1  Jan. 7, 2016

Related U.S. Application Data

(60) Provisional application No. 61/766,600, filed on Feb. 19, 2013.

(51) Int. Cl.
*A61C 8/00* (2006.01)
*H03H 9/215* (2006.01)
(Continued)

(52) U.S. Cl.
CPC ............. *H03H 9/215* (2013.01); *A61C 8/008* (2013.01); *A61C 8/0048* (2013.01);
(Continued)

(58) Field of Classification Search
CPC ......... A61C 1/084; A61C 8/00; A61C 8/0001; A61C 8/0048; A61C 8/0062; A61C 8/008;
(Continued)

(56) References Cited

U.S. PATENT DOCUMENTS 200,445 A  2/1878 Fahnestock
321,847 A  7/1885 Peirce et al.
(Continued)

FOREIGN PATENT DOCUMENTS

CA  2505892  5/2004
JP  2008307281  12/2008
(Continued)

OTHER PUBLICATIONS

USPTO; Non-Final Office Action dated Jan. 5, 2015 in U.S. Appl. No. 12/939,136.
(Continued)

*Primary Examiner* — Nicholas D Lucchesi
(74) *Attorney, Agent, or Firm* — Derrick Harvey, Esq.; Harvey Law

(57) ABSTRACT

A removable system and method for helping position and stabilize implant supported dentures during the healing process after surgery is provided, wherein a removable system comprises a soft tissue supported provisional denture structure configured to help position and stabilize the provisional denture during the transfer of the implant positions to the provisional denture. In the surgical process of providing implant-supported dentures, immediately after the implants are surgically implanted, adhesive is applied to the underside of the provisional denture, and implant connectors are seated on the implants. The provisional denture is seated in the patient's mouth wherein the soft tissue supported provisional denture structure helps stabilize and position the (Continued)

denture. The implant connectors adhere to the adhesive and transfer the implant positions to the provisional denture.

8 Claims, 4 Drawing Sheets

(51) Int. Cl.
    *A61C 13/107* (2006.01)
    *A61C 13/01* (2006.01)

(52) U.S. Cl.
    CPC ........ *A61C 13/0001* (2013.01); *A61C 8/0001* (2013.01); *A61C 13/01* (2013.01)

(58) Field of Classification Search
    CPC ... A61C 8/0089; A61C 13/01; A61C 13/0001; A61C 13/0004; A61B 17/58; A61B 17/62; A61B 17/64
    USPC ........................ 433/167–172; 264/16, 19–20
    See application file for complete search history.

(56) References Cited

U.S. PATENT DOCUMENTS

| | | | |
|---|---|---|---|
| 711,324 | A | 10/1902 | Lacy |
| 1,223,450 | A | 4/1917 | Van Allen |
| 1,293,627 | A | 2/1919 | Bowers |
| 1,585,348 | A | 5/1926 | Hick et al. |
| 1,652,910 | A | 12/1927 | Psayla |
| 1,714,185 | A | 5/1929 | Hugh |
| 1,863,591 | A | 6/1932 | Crowell |
| 1,914,606 | A | 6/1933 | Kinna et al. |
| 2,107,181 | A | 2/1938 | Guyton |
| 2,418,833 | A | 4/1947 | Harris et al. |
| 2,472,492 | A | 6/1949 | Saffir |
| 2,641,835 | A | 6/1953 | Greenmun |
| 2,985,961 | A | 5/1961 | Schwartz |
| 2,994,957 | A | 8/1961 | McLeod |
| 3,083,459 | A | 4/1963 | McMurry et al. |
| 3,241,238 | A * | 3/1966 | Kersten ............... A61C 13/0001 433/171 |
| 3,644,996 | A | 2/1972 | Weinkle |
| 3,667,123 | A | 6/1972 | Huey |
| 3,727,309 | A | 4/1973 | Huey |
| 3,748,739 | A | 7/1973 | Thibert |
| 3,813,777 | A | 6/1974 | Van Handel et al. |
| 3,844,702 | A | 10/1974 | Dimmer et al. |
| 4,029,632 | A | 6/1977 | Gross et al. |
| 4,227,877 | A | 10/1980 | Tureaud et al. |
| 4,247,287 | A | 2/1981 | Gigante |
| 4,299,573 | A | 11/1981 | Ricci |
| 4,533,325 | A * | 8/1985 | Blair .................. A61C 13/1013 433/171 |
| 4,591,341 | A | 5/1986 | Andrews |
| 4,634,377 | A | 1/1987 | Behrend |
| 4,784,608 | A | 11/1988 | Mays |
| 4,931,016 | A | 6/1990 | Sillard |
| 5,098,296 | A | 3/1992 | Cullen |
| 5,151,044 | A | 9/1992 | Rotsaert |
| 5,188,529 | A | 2/1993 | Luth |
| 5,427,906 | A | 6/1995 | Hansen |
| 5,672,305 | A | 7/1997 | Kogure |
| 5,711,668 | A | 1/1998 | Huestis |
| 5,716,214 | A | 2/1998 | Lund |
| 5,718,584 | A | 2/1998 | Wong |
| 5,833,461 | A | 11/1998 | Wong |
| 5,839,900 | A | 11/1998 | Billet et al. |
| 6,056,547 | A | 5/2000 | Names |
| 6,139,322 | A | 10/2000 | Liu |
| 6,149,427 | A | 11/2000 | Van Handel |
| 6,224,372 | B1 | 5/2001 | Ibsen et al. |
| 6,227,851 | B1 | 5/2001 | Chishti |
| 6,384,107 | B2 | 5/2002 | Liu |
| 6,422,864 | B1 | 7/2002 | Glatt |
| 6,488,503 | B1 | 12/2002 | Lichkus et al. |
| 6,616,444 | B2 | 9/2003 | Andreiko et al. |
| 6,851,949 | B1 | 2/2005 | Sachdeva |
| 7,021,934 | B2 | 4/2006 | Aravena |
| 7,153,135 | B1 | 12/2006 | Thomas |
| 7,234,940 | B2 | 6/2007 | Weissman |
| 7,433,810 | B2 | 10/2008 | Pavloskaia et al. |
| 7,474,932 | B2 | 1/2009 | Geng |
| 7,758,345 | B1 | 7/2010 | Christensen |
| 7,806,691 | B2 * | 10/2010 | Berger ................. A61C 13/275 433/167 |
| 8,043,091 | B2 | 10/2011 | Schmitt |
| 8,348,669 | B1 | 1/2013 | Schmitt |
| 8,567,408 | B2 | 10/2013 | Roettger |
| 8,641,938 | B2 | 2/2014 | Howe |
| 8,801,431 | B2 | 8/2014 | Thompson et al. |
| 8,875,398 | B2 | 11/2014 | Balshi et al. |
| 9,055,993 | B2 | 6/2015 | Grobbee et al. |
| 2002/0015934 | A1 | 2/2002 | Rubbert et al. |
| 2002/0180760 | A1 | 12/2002 | Rubbert et al. |
| 2003/0108845 | A1 | 6/2003 | Giovannone |
| 2003/0162147 | A1 | 8/2003 | Dequeker |
| 2003/0163291 | A1 | 8/2003 | Jordan et al. |
| 2003/0211444 | A1 | 11/2003 | Andrews |
| 2004/0005530 | A1 | 1/2004 | Mullaly |
| 2004/0029068 | A1 | 2/2004 | Sachdeva et al. |
| 2004/0219490 | A1 | 11/2004 | Gartner et al. |
| 2005/0175957 | A1 | 8/2005 | Haje |
| 2005/0186539 | A1 | 8/2005 | McLean et al. |
| 2005/0284489 | A1 | 12/2005 | Ambis |
| 2006/0040232 | A1 | 2/2006 | Shoup |
| 2006/0040236 | A1 | 2/2006 | Schmitt |
| 2006/0063135 | A1 | 3/2006 | Mehl |
| 2006/0210945 | A1 | 9/2006 | Savic et al. |
| 2006/0286507 | A1 | 12/2006 | Dequeker |
| 2007/0154868 | A1 | 6/2007 | Scharlack et al. |
| 2007/0231774 | A1 | 10/2007 | Massad |
| 2008/0085489 | A1 | 4/2008 | Schmitt |
| 2008/0090207 | A1 | 4/2008 | Rubbert |
| 2008/0127698 | A1 | 6/2008 | Luckey et al. |
| 2008/0206710 | A1 | 8/2008 | Kruth et al. |
| 2008/0206714 | A1 | 8/2008 | Schmitt |
| 2008/0209974 | A1 | 9/2008 | Ewolski et al. |
| 2008/0300716 | A1 | 12/2008 | Kopelman |
| 2009/0148813 | A1 | 6/2009 | Sun et al. |
| 2009/0162813 | A1 | 6/2009 | Glor |
| 2009/0287332 | A1 | 11/2009 | Adusumilli |
| 2009/0291407 | A1 | 11/2009 | Kuo |
| 2009/0325125 | A1 | 12/2009 | Diangelo |
| 2010/0015572 | A1 | 1/2010 | Dirkes et al. |
| 2010/0062394 | A1 | 3/2010 | Jones et al. |
| 2010/0086186 | A1 | 4/2010 | Zug |
| 2010/0094446 | A1 | 4/2010 | Baloch et al. |
| 2010/0105011 | A1 | 4/2010 | Karkar et al. |
| 2010/0324875 | A1 | 12/2010 | Kalili |
| 2011/0045442 | A1 | 2/2011 | Adusumilli |
| 2011/0112804 | A1 | 5/2011 | Chishti et al. |
| 2011/0129796 | A1 | 6/2011 | Riggio |
| 2011/0236856 | A1 | 9/2011 | Kanazawa et al. |
| 2011/0244417 | A1 | 10/2011 | Hilsen et al. |
| 2012/0058449 | A1 | 3/2012 | Sklarski et al. |
| 2012/0095732 | A1 | 4/2012 | Fisker et al. |
| 2012/0100500 | A1 | 4/2012 | Gao |
| 2012/0178045 | A1 | 7/2012 | Massad |
| 2012/0179281 | A1 | 7/2012 | Steingart et al. |
| 2012/0258426 | A1 | 10/2012 | Boe |
| 2012/0285019 | A1 | 11/2012 | Schechner et al. |
| 2012/0329008 | A1 | 12/2012 | Fishman et al. |
| 2013/0108988 | A1 | 5/2013 | Simoncic |
| 2013/0209962 | A1 | 8/2013 | Thompson et al. |
| 2013/0216978 | A1 | 8/2013 | Thompson et al. |
| 2013/0218532 | A1 | 8/2013 | Thompson et al. |
| 2013/0221554 | A1 | 8/2013 | Jung et al. |
| 2013/0249132 | A1 | 9/2013 | Thompson et al. |
| 2013/0280672 | A1 | 10/2013 | Thompson et al. |
| 2013/0316302 | A1 | 11/2013 | Fisker |
| 2013/0337412 | A1 * | 12/2013 | Kwon .................... A61C 1/082 433/183 |
| 2014/0045967 | A1 | 2/2014 | Thomas et al. |

(56) References Cited

U.S. PATENT DOCUMENTS

| | | | |
|---|---|---|---|
| 2014/0099600 A1* | 4/2014 | Harrison | A61C 8/005 433/173 |
| 2014/0272796 A1 | 9/2014 | Grobbee et al. | |
| 2015/0010885 A1 | 1/2015 | Balshi et al. | |
| 2015/0037760 A1 | 2/2015 | Thompson et al. | |
| 2015/0064653 A1 | 3/2015 | Grobbee et al. | |
| 2015/0134094 A1 | 5/2015 | Thompson et al. | |
| 2015/0230891 A1 | 8/2015 | Grobbee et al. | |
| 2015/0245891 A1 | 9/2015 | Grobbee | |
| 2015/0245892 A1 | 9/2015 | Grobbee | |

FOREIGN PATENT DOCUMENTS

| | | |
|---|---|---|
| WO | 2001032096 | 12/2001 |
| WO | 2009105661 | 8/2009 |
| WO | 2009105700 | 8/2009 |
| WO | 2010022479 | 3/2010 |
| WO | 2012041329 | 4/2012 |
| WO | 2012061652 | 5/2012 |
| WO | 2012061655 | 5/2012 |
| WO | 2012061659 | 5/2012 |
| WO | 2012061660 | 5/2012 |
| WO | 2014130536 | 8/2014 |
| WO | 2014159436 | 10/2014 |
| WO | 2015031062 | 3/2015 |

OTHER PUBLICATIONS

USPTO; Final Office Action dated Sep. 25, 2015 in U.S. Appl. No. 12/939,136.
USPTO; Non-Final Office Action dated Apr. 9, 2015 in U.S. Appl. No. 12/939,138.
USPTO; Final Office Action dated Aug. 19, 2015 in U.S. Appl. No. 12/939,138.
USPTO; Office Action dated Sep. 24, 2013 in U.S. Appl. No. 13/249,210.
USPTO; Final Office Action dated Mar. 6, 2014 in U.S. Appl. No. 13/249,210.
USPTO; Notice of Allowance dated Jun. 6, 2014 in U.S. Appl. No. 13/249,210.
USPTO; Restriction Requirement dated Feb. 12, 2015 in U.S. Appl. No. 13/369,238.
USPTO; Non-Final Office Action dated Sep. 21, 2015 in U.S. Appl. No. 13/369,238.
USPTO; Restriction Requirement dated Dec. 23, 2013 in U.S. Appl. No. 13/823,466.
USPTO; Non-Final Office Action dated Jun. 6, 2014 in U.S. Appl. No. 13/823,466.
USPTO; Final Office Action dated Mar. 26, 2015 in U.S. Appl. No. 13/823,466.
USPTO; Restriction Requirement dated Sep. 5, 2014 in U.S. Appl. No. 13/823,621.
USPTO; Non-Final Office Action dated Oct. 23, 2014 in U.S. Appl. No. 13/823,621.
USPTO; Notice of Allowance dated Jun. 22, 2015 in U.S. Appl. No. 13/823,621.
USPTO; Notice of Allowance dated Aug. 24, 2015 in U.S. Appl. No. 13/823,662.
USPTO; Non-Final Office Action dated Jun. 20, 2014 in U.S. Appl. No. 13/830,963.
USPTO; Final Office Action dated dated Nov. 7, 2014 in U.S. Appl. No. 13/830,963.
USPTO; Non-Final Office Action dated Aug. 13, 2015 in U.S. Appl. No. 13/830,963.
USPTO; Non-Final Office Action dated Dec. 19, 2014 in U.S. Appl. No. 14/013,295.
USPTO; Notice of Allowance dated Apr. 13, 2015 in U.S. Appl. No. 14/013,295.
USPTO; Restriction Requirement dated Jul. 2, 2014 in U.S. Appl. No. 14/195,348.
USPTO; Office Action dated Aug. 21, 2014 in U.S. Appl. No. 14/195,348.
USPTO; Final Office Action dated Oct. 21, 2014 in U.S. Appl. No. 14/195,348.
USPTO; Non-Final Office Action dated Aug. 11, 2015 in U.S. Appl. No. 14/195,348.
PCT; International Search Report and Written Opinion dated Jul. 18, 2012 in Application No. PCT/US2011/059230.
PCT; International Preliminary Report on Patentability dated May 8, 2013 in Application No. PCT/US2011/059230.
PCT; International Search Report and Written Opinion dated Jul. 18, 2012 in Application No. PCT/US2011/059235.
PCT; International Preliminary Report on Patentability dated May 8, 2013 in Application No. PCT/US2011/059235.
PCT; International Search Report and Written Opinion dated Jul. 9, 2012 in Application No. PCT/US2011/059239.
PCT; International Preliminary Report on Patentability dated May 8, 2013 in Application No. PCT/US2011/059239.
PCT; International Search Report and Written Opinion dated Jul. 18, 2012 in Application No. PCT/US2011/059240.
PCT; International Preliminary Report on Patentability dated May 8, 2013 in Application No. PCT/US2011/059240.
PCT; International Search Report and Written Opinion dated Jul. 25, 2014 in Application No. PCT/US2014/017136.
PCT; International Search Report and Written Opinion dated Aug. 7, 2014 in Application No. PCT/US2014/023654.
EPO; European Search Report dated Mar. 4, 2014 in Application No. 11838839.6.
EPO; European Search Report and Opinion dated Mar. 3, 2014 in Application No. 11838843.8.
EPO; Extended European Search Report dated Jun. 18, 2015 in Application No. 15156818.5.
U.S. Appl. No. 13/823,466, filed Mar. 14, 2013, System and Process for Duplication of Dentures.
U.S. Appl. No. 12/939,136, filed Nov. 3, 2010, System and Process for Duplication of Dentures.
U.S. Appl. No. 13/823,621, filed Mar. 14, 2013, Systems and Process for Forming Anatomical Features in Dentures.
U.S. Appl. No. 12/939,138, filed Nov. 3, 2010, Systems and Process for Forming Anatomical Features in Dentures.
U.S. Appl. No. 14/798,717, filed Jul. 14, 2015, Systems and Process for Forming Anatomical Features in Dentures.
U.S. Appl. No. 13/823,662, filed Mar. 14, 2013, System and Process for Optimization of Dentures.
U.S. Appl. No. 12/939,141, filed Nov. 3, 2010, System and Process for Optimization of Dentures.
U.S. Appl. No. 13/249,210 U.S. Pat. No. 8,801,431, filed Sep. 29, 2011 Aug. 12, 2014, Combination Tool for Anatomical Measurement for Denture Manufacture.
U.S. Appl. No. 13/369,238, Feb. 8, 2012, Process and Systems for Molding Thermosetting Plastics.
U.S. Appl. No. 13/830,963, filed Mar. 14, 2013, System and Process for Manufacturing of Dentures.
U.S. Appl. No. 14/013,295, filed Aug. 29, 2013, Improved Denture Reference and Registration System.
U.S. Appl. No. 13/830,963, Apr. 28, 2015, Denture Reference and Registration System.
U.S. Appl. No. 14/195,348, Mar. 3, 2014, System and Method for Manufacturing Layered Dentures.
U.S. Appl. No. 14/506,338, filed Oct. 3, 2014, System and Method for Manufacturing Layered Dentures.
U.S. Appl. No. 14/821,097, Aug. 7, 2015, System and Method for Manufacturing Layered Dentures.

* cited by examiner

REMOVABLE SYSTEM AND METHOD FOR DENTURES AND SURGICAL GUIDES

FIELD OF INVENTION

The present invention relates to implant-supported dentures. More particularly, the present invention relates to a removable system and method for dentures during the healing process after surgery for such implant-supported dentures.

BACKGROUND OF THE INVENTION

In the field of dentures, one difficulty faced by dental surgeons is when a patient does not possess sufficient teeth in the jaw, but has enough bone in the jaw to support implants. A regular denture rests on the gums, and is not supported by implants. In some instances, an implant-supported denture is used, which is a type of denture that is supported by and attached to the implants. An implant-supported denture has special attachments that affix onto attachments on the implants.

Implant-supported dentures usually are made for the lower jaw because regular dentures tend to be less stable there. Usually, a regular denture made to fit an upper jaw is quite stable on its own and does not need the extra support offered by implants. However, a patient can receive an implant-supported denture in either the upper or lower jaw. In some instances, an implant-supported denture is utilized because the bone and tissue structure of the patient is not well-suited to stably retain a non-implant-supported denture.

In some instances, surgery is required for bone reduction where the denture system will not suitably fit on the patients jaw and gums. Unfortunately, it can be difficult to accurately reduce a patient's bone, for example, by using a convention denture baseplate as a trimming guide, as it prohibits access to the area needing reduction. Traditionally, a medical professional would grind the patient's bone, then test fit the denture system in an iterative process of grinding and test fitting.

Furthermore, the fitting of a conventional implant-supported denture is often difficult and inaccurate due to the need to fit the denture quickly because the patient is experiencing post-operation pain. For example, a conventional implant-supported denture may be fitted immediately following the implant surgery. In some instances, this fitting involves trimming along the border of the denture for hygienic reasons, for example, so food will not be trapped behind the denture base. Conventional implant-supported dentures often must be trimmed by grinding or cutting wherein the medical professional must test fit the denture repeatedly during the grinding or cutting process, prolonging the fitting and in some instances, exacerbating patient pain. Medical professionals fitting a conventional implant-supported denture also risk overtrimming the denture during the grinding or cutting process. Similar difficulties confront a medical professional performing a conventional bone reduction procedure. The procedure is often inaccurate and risks overtrimming due to the necessity of repeated trial fitting of the denture system or conventional denture baseplate.

SUMMARY OF THE INVENTION

In accordance with various aspects of the present invention, a removable system and method for helping position and stabilize implant supported dentures during the healing process after surgery is provided. In accordance with an exemplary embodiment, a removable system comprises a soft tissue supported provisional denture structure configured to help position and stabilize the provisional denture during the transfer of the implant positions to the provisional denture. In the surgical process of providing implant-supported dentures, immediately after the implants are surgically implanted, adhesive is applied to the underside of the provisional denture, and implant connectors are seated on the implants. The provisional denture is seated in the patient's mouth wherein the soft tissue supported provisional denture structure helps stabilize and position the denture. The implant connectors adhere to the adhesive and transfer the implant positions to the provisional denture. In some example embodiments, said adhesive is a polymer.

In an exemplary embodiment, the provisional denture comprises a soft tissue supported structure attached to the provisional denture by connectors. The soft tissue supported structure of the provisional denture is configured to be cut or broken off by way of the connectors at the location of coupling, allowing for the provisional denture to be trimmed down along its border and thus be ready to stay in the patient's mouth as a provisional implant supported denture. In accordance with an exemplary embodiment, the pattern and shape of the connectors at the location of the coupling is designed to conform to the individual patient's anatomy to facilitate rapid trimming by the medical professional and accurate fitting to the individual patient's anatomy. As a result, patient discomfort can be minimized.

In accordance with one example embodiment of the provisional denture system, the provisional denture system may further comprise a bar structure interfaced between the implants and the denture, provisional or final, in order to provide enhanced rigidity and stability to the denture, provisional or final. In accordance with one example embodiment, the denture is installed without the bar structure, until such time as the patient has healed from the surgery sufficiently that the inflammation or swelling of the patient's soft tissue has receded sufficiently to allow the bar structure to fit beneath the denture.

In accordance with other exemplary embodiments, an alternative application for the cut or break away removable feature is with a surgical bone reduction guide when bone reduction is needed. In such an embodiment, a cut or break away section can be configured within a denture baseplate, and then can be removed by cutting or breaking away one or more connectors to create an access opening to grind the bone. In accordance with an exemplary embodiment, the pattern and shape of the connectors is designed to conform to the individual patient's anatomy to facilitate rapid and accurate grinding of the bone. In accordance with an exemplary embodiment, a medical professional may elect to not break away the one or more connectors to create an access opening to grind the bone, and may instead elect to repeatedly test fit the denture baseplate while grinding the bone. In accordance with an exemplary embodiment, the baseplate may be transparent in order to permit easy comparison of the bone to the baseplate during the grinding process.

BRIEF DESCRIPTION OF THE DRAWINGS

A more complete understanding of the present invention may be derived by referring to the detailed description and claims when considered in connection with the Figures, where like reference numbers refer to similar elements throughout the Figures, and:

DETAILED DESCRIPTION OF EXEMPLARY EMBODIMENTS OF THE INVENTION

The present invention may be described herein in terms of various components and operating or surgical steps. It should be appreciated that such components and steps may be realized by any number of structural materials and components configured to perform the specified functions. For example, the present invention may employ various tools, devices and instruments, which may carry out a variety of functions under the control of one or more control systems, microprocessors or other control devices, or are manually operated by the surgeon. In addition, the present invention may be practiced in any number of dental contexts and the exemplary embodiments relating to a removable system and method for dentures during the healing process after surgery for implant-supported dentures are merely a few of the exemplary applications for the invention. For example, the principles, features and methods discussed may be applied to any orthodontic or dental treatment application.

In accordance with various aspects of the present invention, a removable system and method for helping position and stabilize implant supported dentures during the healing process after surgery is provided. In accordance with an exemplary embodiment, a removable system comprises a soft tissue supported provisional denture configured to help position and stabilize the implant supported denture during the transfer of the implant positions. In the surgical process of providing implant supported dentures, immediately after the implants are placed, the provisional denture is seated on the implants, wherein the implant positions may be transferred to the provisional denture.

In an exemplary embodiment, the provisional denture comprises a soft tissue supported structure attached to the provisional denture by connectors. The soft tissue supported structure of the provisional denture is configured to be cut or broken off by way of the connectors at the location of coupling, allowing for the provisional denture to be trimmed down along its border and thus be ready to stay in the patient's mouth as a provisional implant supported denture during the healing period.

Figure 1:
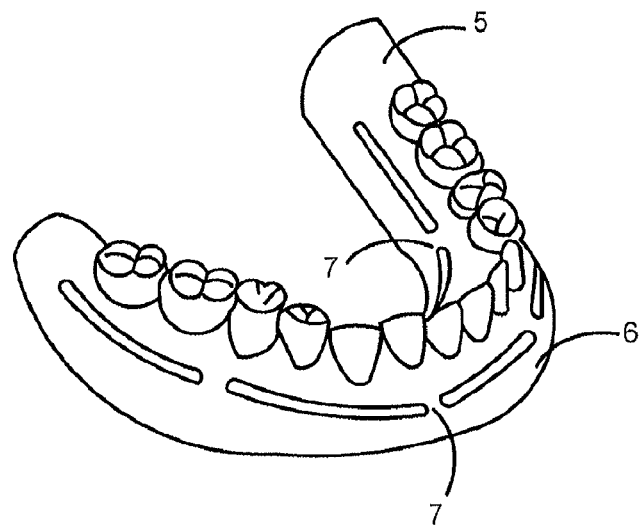
FIG. 1 is a perspective view of a provisional denture having a soft tissue supported structure in accordance with an exemplary embodiment of the present invention.
Figure 2:
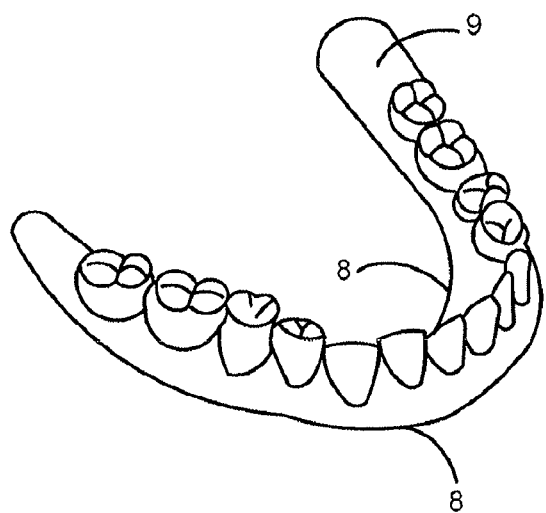
FIG. 2 is a perspective view of a final denture after removal of the soft tissue supported structure in accordance with an exemplary embodiment of the present invention.

For example, with reference to an exemplary embodiment illustrated in FIG. 1, a soft tissue supported provisional denture 5 includes a remaining portion (in this example, the top portion further illustrated in the lower jaw provisional denture of FIG. 2) comprising denture materials with denture teeth, coupled or attached to a soft tissue supported structure 6 by one or more connectors 7. Provisional denture 5 can made with any conventional dental structure or material used in implant-supported denture applications currently or hereafter devised. Provisional denture 5 can be made with any manufacturing process suitable for an intended structure or material, such as, a CAD/CAM denture fabrication process, or a traditional denture fabrication processes, or any process currently or hereinafter devised. For example, in accordance with various exemplary embodiments, provisional denture 5 can be made with processes described in U.S. application Ser. No. 12/939,141, entitled System and Processes for Optimization of Dentures, and in U.S. application Ser. No. 12/939,138, entitled System and Processes for Anatomical Features in Dentures.

Soft tissue supported structure 6 is configured to temporarily facilitate alignment of provisional denture 5 onto the gums and jawbone of the patient, for example, to help position and stabilize the provisional denture during the transfer of the implant positions to the provisional denture prior to connection of the provisional denture to the implants. Soft tissue supported structure 6 is configured to facilitate alignment and position. The soft tissue supported structure is configured to be cut or broken off by way of the connectors 7 at the location of coupling, allowing for the provisional denture to be quickly trimmed down along its border and thus be ready to stay in the patient's mouth as a provisional implant supported denture. In accordance with an exemplary embodiment, the pattern and shape of the connectors at the location of the coupling is designed to conform to the individual patient's anatomy to facilitate rapid trimming by the medical professional and accurate fitting to the individual patient's anatomy. Furthermore, the open space between connectors 7 can permit the medical professional to view the alignment of provisional denture 5 and soft tissue supported structure 6 with respect to the patient's gums and jawbone.

One or more connectors 7 can comprise a thin or narrow portion or may comprise a wide or thick portion. In some embodiments, a provisional denture 5 having a soft tissue supported structure 6 may comprise one or more connectors 7 of differing dimensions and spacing.

In the process of implant-supported dentures, immediately after the implants are surgically implanted, a provisional denture (FIG. 1) is seated on the implants. The implant positions need to be transferred to the provisional denture. The initial seating and transfer of the implant positions can be readily facilitated with the soft tissue supported provisional denture 5, wherein the soft tissue supported structure 6 enables movement of the provisional denture to the desired position and further stabilizes the denture during the transfer to the implant positions.

After the transfer of the implant positions is finished, the soft tissue supported structure 6 of the provisional denture connected by the connectors 7 will be trimmed, cut, or broken off. Such cutting or breaking away can be done manually be flexing the soft tissue supported structure at the connection to connectors 7, or by using any knife, scalpel, saw, grinding wheel, sandpaper, or other tool adaptably suited to such trimming, cutting, or breaking. After trimming, cutting, or breaking away the removable tissue supported structure 6 of the provisional denture the provisional denture with the trimmed down border 8 (FIG. 2) is ready to stay in the patient's mouth as a provisional implant supported denture 9 during the healing period.

Figure 5:
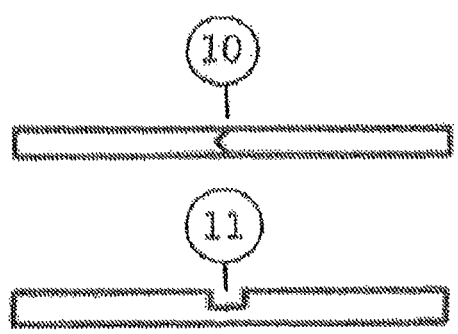
FIG. 5 is a side view of exemplary connector interfaces for coupling the soft tissue supported structure of the provisional denture or for coupling the cut or break away section within an exemplary bone reduction guide in accordance with an exemplary embodiment of the present invention.
Figure 6:
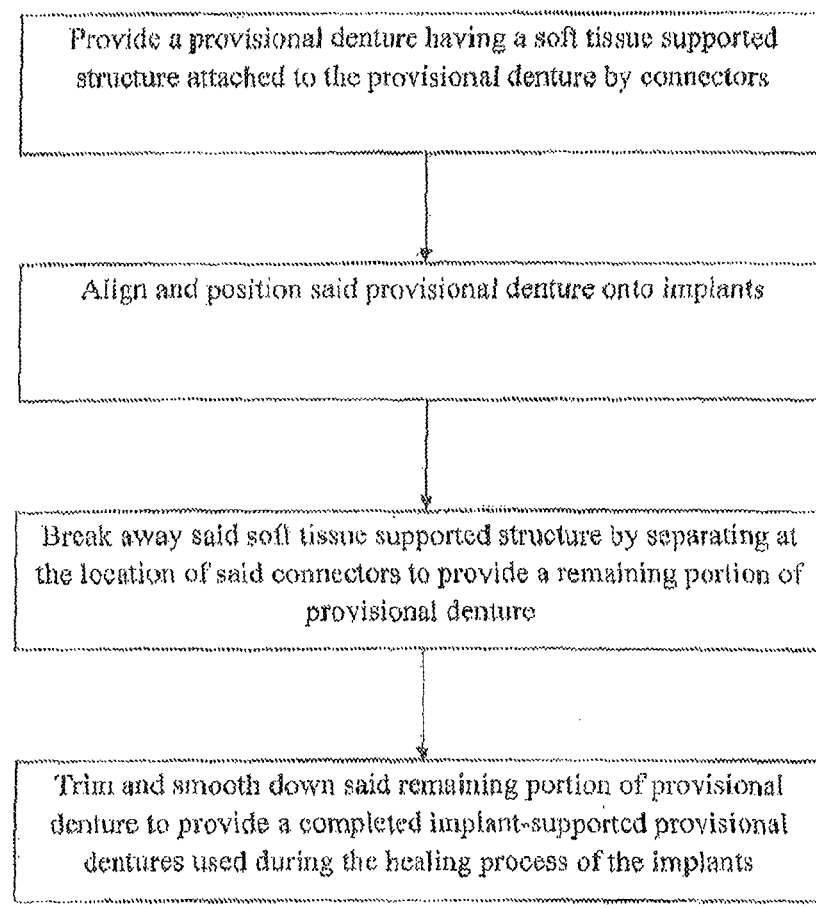
FIG. 6 is a flow chart illustrating an exemplary process for denture treatment with implant-supported dentures in accordance with an exemplary embodiment of the present invention.

To further facilitate the cutting or breaking away of soft tissue supported structure, in accordance with an exemplary embodiment, one or more connectors 7 (FIG. 1) or connectors 1 (FIG. 3) can include an interface configured to facilitate easier separation from the remaining portion of provisional denture 5. For example, with reference to FIG. 5, one or more connectors can comprise a snap connection 10, a break line 11, or any other perforations configured to facilitate the cutting or breaking away functions.

With reference to FIG. 2, after cutting or breaking away the removable tissue supported structure 6 of the provisional denture, the remaining portion of provisional denture 5 will include a trimmed down border 8 suitable to remain in the patient's mouth as a completed provisional implant supported denture 9 during the healing period. The trimming down of border 8 can be conducted by any conventional procedure for trimming or smoothing dentures.

Figure 3:
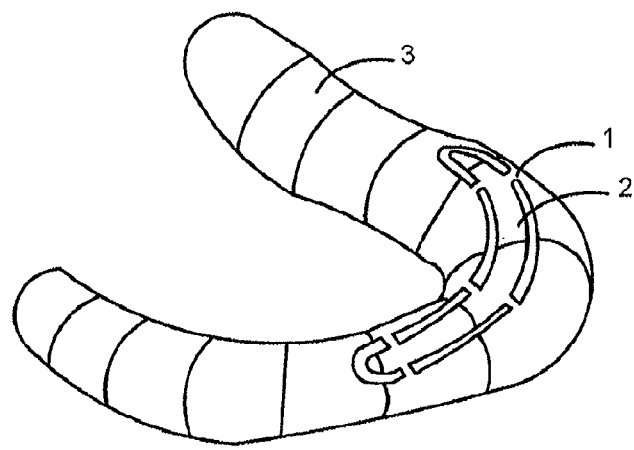
FIG. 3 is a perspective view of a surgical bone reduction guide in accordance with an exemplary embodiment of the present invention.
Figure 4:
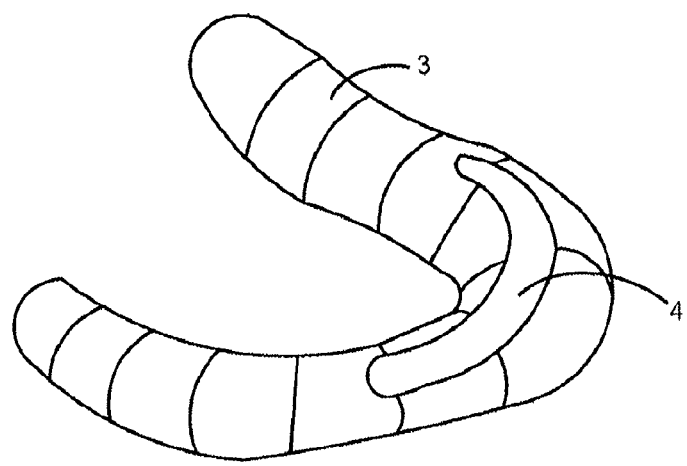
FIG. 4 is a perspective view of a surgical bone reduction guide having removed a connected portion in accordance with an exemplary embodiment of the present invention.

An alternative application for the cut or break away removable system is the bone reduction guide (FIGS. 3 and 4). If bone reduction is needed, a cut or break away section 2 in a denture baseplate 3 can be removed by cutting or breaking away the connectors 1 to create an access hole 4 to grind the bone. In some embodiments, access hole 4 is designed to conform to the individual patient's anatomy in order to facilitate accurate and rapid bone grinding.

In some instances of implant supported dentures, surgery is required for bone reduction where the denture will not suitably fit on the patients jaw and gums. In accordance with another exemplary embodiment, the cut or break away removable feature utilized with soft tissue supported structure 6 and connectors 7 (FIGS. 1 and 2) can also be implemented with a surgical bone reduction guide when bone reduction is needed. In an embodiment, a cut or break away section can be configured within a denture baseplate, and then can be removed by cutting or breaking away one or more connectors to create an access opening to grind the bone. For example, with reference to FIG. 3, a bone reduction guide can comprise a denture baseplate 3 having a cut or break away removable portion 2 within a denture baseplate 3. Cut or break away portion 2 is suitably configured in size based on the portion of bone that will be ground down, and is connected to denture baseplate 3 through one of more connectors 1. If bone reduction is needed, cut or break away section 2 can be removed by cutting or breaking away the connectors 1 to create an access opening 4 to grind the bone.

In accordance with an exemplary embodiment, the pattern and shape of the connectors is designed to conform to the individual patient's anatomy to facilitate rapid and accurate grinding of the bone. In accordance with an exemplary embodiment, a medical professional may elect to not break away the one or more connectors to create an access opening to grind the bone, and may instead elect to repeatedly test fit the denture baseplate while grinding the bone. In accordance with an exemplary embodiment, the baseplate may be transparent in order to permit easy comparison of the bone to the baseplate during the grinding process.

Benefits, other advantages, and solutions to problems have been described herein with regard to specific embodiments. However, the benefits, advantages, solutions to problems, and any element(s) that may cause any benefit, advantage, or solution to occur or become more pronounced are not to be construed as critical, required, or essential features or elements of any or all the claims or the invention. The scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described exemplary embodiments that are known to those of ordinary skill in the art are expressly incorporated herein by reference and are intended to be encompassed by the present claims.

The invention claimed is:

1. A method for facilitating position and stabilization of implant supported provisional dentures, said method comprising:
   providing a provisional denture having a soft tissue supported structure attached to the provisional denture by connectors;
   aligning and positioning said provisional denture onto implants;
   breaking away said soft tissue supported structure by separating at the location of said connectors to provide a remaining portion of provisional denture; and
   trimming and smoothing down said remaining portion of provisional denture to provide completed implant-supported provisional dentures used during a healing process of the implants.

2. The method of claim 1 wherein said provisional denture is defined and manufactured using CAD/CAM technology.

3. The method of claim 1 wherein the steps are performed when implants are surgically implanted into a patient.

4. The method of claim 1, the step of providing a provisional denture having a soft tissue supported structure attached to the provisional denture by connectors further comprising said connectors having differing dimensions or spacing.

5. The method of claim 1, the step of providing a provisional denture having a soft tissue supported structure attached to the provisional denture by connectors further comprising said connectors having similar dimensions or spacing.

6. The method of claim 1, the step of providing a provisional denture having a soft tissue supported structure attached to the provisional denture by connectors further comprising said connectors having an interface to facilitate separation.

7. The method of claim 1, the step of providing a provisional denture having a soft tissue supported structure attached to the provisional denture by connectors further comprising said connectors having a pattern and shape conforming to an individual patient's anatomy.

8. The method of claim 1 further comprising a step of viewing the alignment of the provisional denture and soft tissue supported structure through open spaces between the connectors.

* * * * *